US007056727B2

(12) United States Patent
Saint-Ramon et al.

(10) Patent No.: US 7,056,727 B2
(45) Date of Patent: Jun. 6, 2006

(54) STRAW FOR THE CONSERVATION OF SMALL QUANTITIES OF SUBSTANCES, IN PARTICULAR BIOLOGICAL LIQUIDS

(75) Inventors: Jean-Gérard Saint-Ramon, L'Aigle (FR); Francis Lesieur, Saint-Michel Thubeuf (FR)

(73) Assignee: IMV Technologies, L'Aigle (FR)

( * ) Notice: Subject to any disclaimer, the term of this patent is extended or adjusted under 35 U.S.C. 154(b) by 488 days.

(21) Appl. No.: 10/139,627

(22) Filed: May 7, 2002

(65) Prior Publication Data

US 2002/0183653 A1 Dec. 5, 2002

(30) Foreign Application Priority Data

May 7, 2001 (FR) .................................. 01 06080

(51) Int. Cl.
*C12M 1/24* (2006.01)
*C12M 3/00* (2006.01)

(52) U.S. Cl. .............................. 435/307.1; 435/304.1; 435/309.1; 422/100; 422/102; 73/864.02; 73/864.03; 220/364; 600/33

(58) Field of Classification Search ............ 435/284.1, 435/304.1, 304.2, 307.1; 422/100, 102, 916, 422/917; 73/864.02, 864.03; 215/261; 220/364, 220/371; 600/33–35, 573
See application file for complete search history.

(56) References Cited

U.S. PATENT DOCUMENTS

| | | | | |
|---|---|---|---|---|
| 4,925,060 | A * | 5/1990 | Gustafson | 220/371 |
| 5,279,606 | A | 1/1994 | Haber et al. | |
| 6,203,489 | B1 | 3/2001 | Mori et al. | |
| 6,300,125 | B1 * | 10/2001 | Saint-Ramon et al. | 435/307.1 |

FOREIGN PATENT DOCUMENTS

| | | | |
|---|---|---|---|
| EP | 0 917 862 | A1 | 5/1999 |
| FR | 2 753 367 | A1 | 3/1998 |
| GB | 669265 | | 4/1952 |
| GB | 1299934 | A | 12/1972 |
| JP | 07-22717 | | 4/1995 |
| JP | 08-862 | | 5/1996 |
| WO | WO 87/00439 | A1 | 1/1987 |

* cited by examiner

*Primary Examiner*—William H. Beisner
(74) *Attorney, Agent, or Firm*—Browdy and Neimark, PLLC

(57) ABSTRACT

A straw (1) for the conservation of small quantities of substances, in particular biological substances, the straw having a segment of tube (2) provided, inside one end, with a stopper (3) including gel powder, characterized in that the straw stopper includes a thermoplastics material core (4) sheathed with filaments constituting a sheath (5). The straw of the invention absorbs only a very small amount of the liquid contained therein.

17 Claims, 2 Drawing Sheets

STRAW FOR THE CONSERVATION OF SMALL QUANTITIES OF SUBSTANCES, IN PARTICULAR BIOLOGICAL LIQUIDS

The present invention relates to a straw for the conservation of small quantities of substances, in particular biological liquids.

This type of straw, which is known as a "French straw", was disclosed for the first time in French patent No. 995 878.

Straws manufactured in accordance with the above patent and used until now have a three-part stopper consisting of two plugs of a fibrous substance with a powder between them that on contact with a liquid is converted into an impermeable gel or paste adhering to the wall of the tube to create a sealed stopper.

Straws with a three-part stopper developed and marketed by the applicant are entirely satisfactory. Nevertheless, some absorption of the liquid contained in the straw has been noted, although it is very slight, of the order of 7%.

One solution to the above problem that has been proposed is to replace the three-part stopper with a metal or rigid plastics material ball. This solution has not proved satisfactory because, although absorption of the liquid contained in the straw has been eliminated, new and unacceptable difficulties have arisen, the stopper no longer providing a liquid seal.

The patent FR-A-2 753 367 proposes a straw including a three-part stopper comprising a hydrogel powder between two plugs, namely an external plug and an internal plug, said straw being characterized in that the length of the external plug is at least twice the length of the internal plug. According to the above patent, absorption of the liquid contained in the straw is only very slightly reduced compared to that observed in a straw fitted with a standard three-part stopper.

An object of the present invention is to provide a straw fitted with a stopper that absorbs only a small quantity of a liquid contained in the straw. To be more precise, an object of the invention is to provide a straw fitted with a stopper that absorbs a quantity of a liquid contained therein at most equal to approximately 4%.

Other objects and advantages of the invention will become apparent on reading the following description.

The present invention conforms to the above object and provides a straw for the conservation of small quantities of substances, in particular biological substances, said straw comprising a segment of tube provided, inside one end, with a stopper including gel powder, characterized in that said straw stopper includes a thermoplastics material core sheathed with filaments constituting a sheath.

The filaments are preferably synthetic filaments, for example polyester filaments.

The gel powder is a material adapted to be converted on contact with a liquid into an impermeable gel or paste adhering to the wall of the tube to create a sealed stopper.

The gel powder can be an alginate or polyvinyl alcohol, for example.

The sheath can take the form of a braid.

The braid in accordance with the present invention can be manufactured by braiding, knitting, weaving or wrapping filaments, for example synthetic filaments, on an extruded thermoplastics material core.

The filaments of the sheath can be treated to render them hydrophilic or hydrophobic. They are white or colored; in the latter case, the filaments of the sheath constitute a color-coded indicator of the contents of the straw.

The core can also be colored, also constituting in this case a color-coded indicator of the contents of the straw.

Similarly, the gel powder can also be colored, also constituting in this case a color-coded indicator of the contents of the straw.

The filaments can be fixed to the core by tension or by means of an adhesive. A thin thermoplastics material sheath can cover everything.

In accordance with the invention, the straw can be fitted with a three-part stopper or a one-piece stopper.

In a first embodiment of the invention, the stopper of the straw according to the invention is a three-part stopper.

It comprises three parts of substantially the same length or different lengths.

The external part, which is not in direct contact with the liquid contained in the straw, comprises a thermoplastics material core sheathed by filaments, for example synthetic filaments.

The internal part, which is in contact with the liquid contained in the straw, is a thermoplastics material core sheathed with filaments, for example synthetic filaments.

The intermediate part comprises gel powder.

In a second embodiment of the invention, the stopper of the straw according to the invention is a three-part stopper.

It comprises three parts of substantially the same length or different lengths.

The external part, which is not in direct contact with the liquid contained in the straw, is a plug, for example a braid, of a standard fibrous substance, for example viscose polyester.

The internal part, which is in contact with the liquid contained in the straw, comprises a thermoplastics material core sheathed with filaments, for example synthetic filaments.

The intermediate part comprises gel powder.

In a third embodiment, the stopper of the straw according to the invention is a three-part stopper.

It comprises three parts of substantially the same length or different lengths.

The external part, which is not in direct contact with the liquid contained in the straw, is a plug, for example a braid, of a standard fibrous substance, for example viscose polyester.

The internal part, which is in contact with the liquid contained in the straw, comprises a thermoplastics material core sheathed with filaments, for example synthetic filaments, said core incorporating a bore.

The intermediate part comprises gel powder.

In a fourth embodiment, the stopper of the straw according to the invention is a three-part stopper.

It comprises three parts of substantially the same length or different lengths.

The external part, which is not in direct contact with the liquid contained in the straw, is a plug, for example a braid, of a standard fibrous substance, for example viscose polyester.

The internal part, which is in contact with the liquid contained in the straw, comprises a thermoplastics material core sheathed with filaments, for example synthetic filaments, said core including a central braid of hydrophilic or hydrophobic filaments.

The intermediate part comprises gel powder.

In the case of a three-part stopper, the total length of the stopper is from approximately 7 mm to approximately 14 mm.

The external part has a length from approximately 3 mm to approximately 6 mm.

The internal part has a length from approximately 2 mm to approximately 5 mm.

The intermediate part has a length from approximately 1.5 mm to approximately 3 mm.

In a fifth embodiment, the stopper of the straw according to the invention is a one-piece stopper and comprises a thermoplastics material core sheathed with filaments, for example synthetic filaments. The filaments of the sheath are impregnated with gel powder.

In a sixth embodiment, the stopper of the straw according to the invention is a one-piece stopper and comprises a thermoplastics material core sheathed with filaments, for example synthetic filaments, and includes a central braid of hydrophilic or hydrophobic filaments impregnated with gel powder.

The length of the one-piece stopper according to the invention is from approximately 5 mm to approximately 14 mm.

The straw of the invention suffers very little absorption of the liquid contained therein, of the order of 4% and even less.

The invention will be described in more detail but in a nonlimiting manner with reference to the accompanying drawings, in which.

Figure 1:
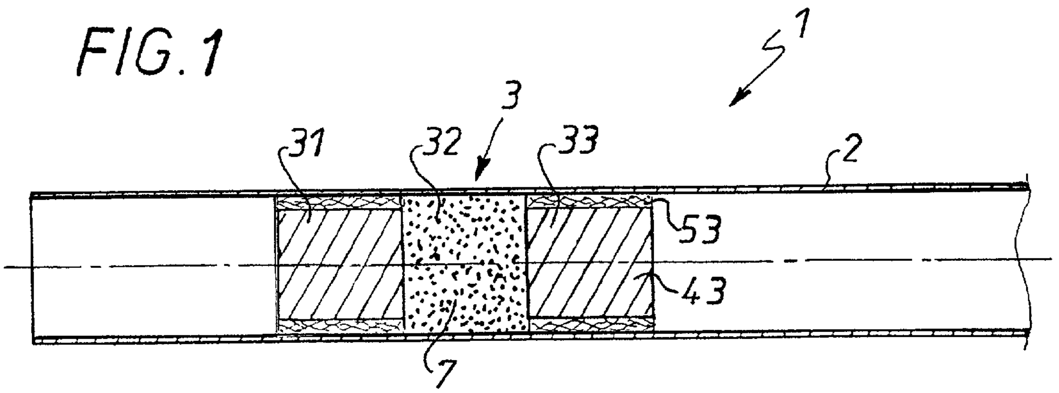
FIG. 1 is a partial view of a first embodiment of a straw of the invention.

Referring to FIG. 1, the straw 1 comprises a segment of tube 2 provided at one end with a three-part stopper 3.

The external part 31, which is not in contact with the liquid contained in the straw, comprises a thermoplastics material core 43 sheathed with filaments in the form of a sheath 53.

The internal part 33, which is in contact with the liquid contained in the straw, comprises a thermoplastics material core 43 sheathed with filaments in the form of a sheath 53.

The intermediate part 32 comprises gel powder 7.

Figure 2:
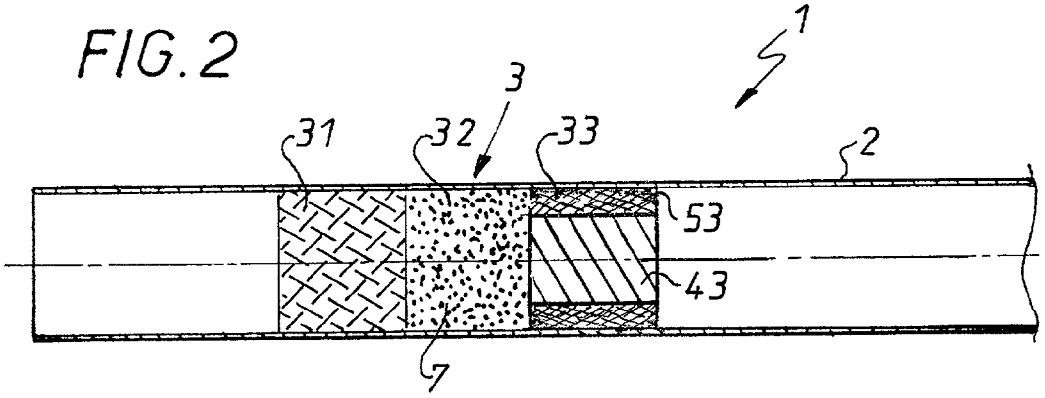
FIG. 2 is a partial view of a second embodiment of a straw of the invention.

Referring to FIG. 2, the straw 1 comprises a segment of tube 2 provided at one end with a three-part stopper 3.

The external part 31, which is not in contact with the liquid contained in the straw, is a braid made from a fibrous substance.

The internal part 33, which is in contact with the liquid contained in the straw, comprises a thermoplastics material core 43 sheathed with filaments in the form of a sheath 53.

The intermediate part 32 comprises gel powder 7.

Figure 3:
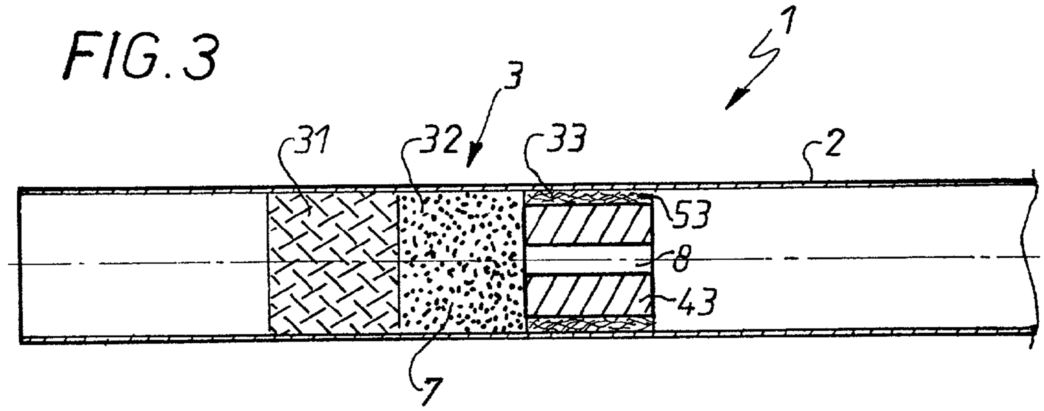
FIG. 3 is a partial view of a third embodiment of a straw of the invention.

Referring to FIG. 3, the straw 1 comprises a segment of tube 2 provided at one end with a three-part stopper 3.

The external part 31, which is not in contact with the liquid contained in the straw, is a braid made from a fibrous substance.

The internal part 33, which is in contact with the liquid contained in the straw, comprises a thermoplastics material core 43 sheathed with filaments in the form of a sheath 53. The core 43 includes a bore 8.

The intermediate part 32 comprises gel powder 7.

Figure 4:
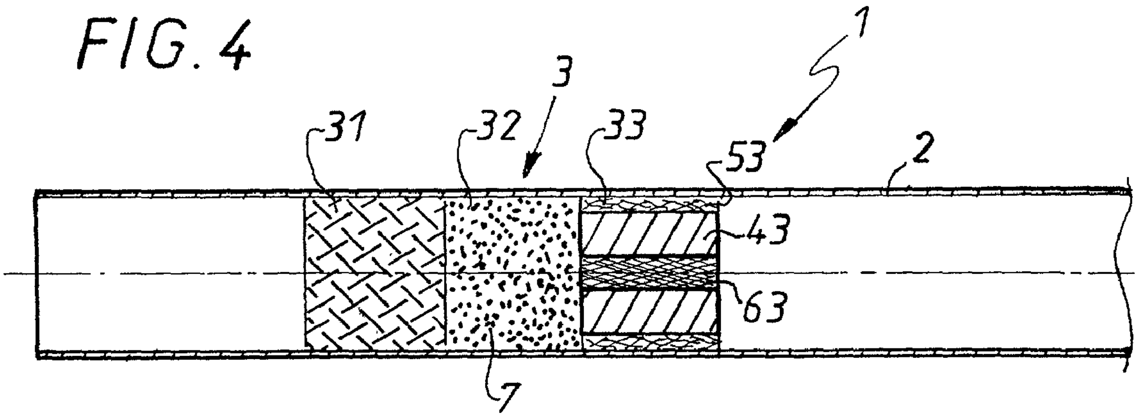
FIG. 4 is a partial view of a fourth embodiment of a straw of the invention.

Referring to FIG. 4, the straw 1 comprises a segment of tube 2 provided at one end with a three-part stopper 3.

The external part 31, which is not in contact with the liquid contained in the straw, is a braid made from a fibrous substance.

The internal part 33, which is in contact with the liquid contained in the straw, comprises a thermoplastics material core 43 sheathed with filaments in the form of a sheath 53. The core 43 includes a central braid 63.

The intermediate part 32 comprises gel powder 7.

Figure 5:
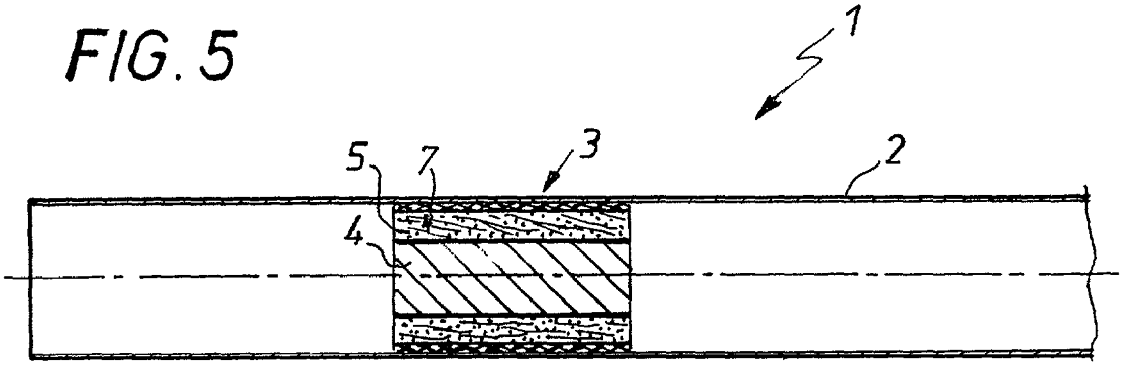
FIG. 5 is a partial view of a fifth embodiment of a straw of the invention.

Referring to FIG. 5, the straw 1 comprises a segment of tube 2 fitted at one end with a one-piece stopper 3.

The stopper 3 comprises a thermoplastics material core 4 sheathed with filaments constituting a sheath 5. The filaments of the sheath 5 are impregnated with a gel powder 7.

Figure 6:
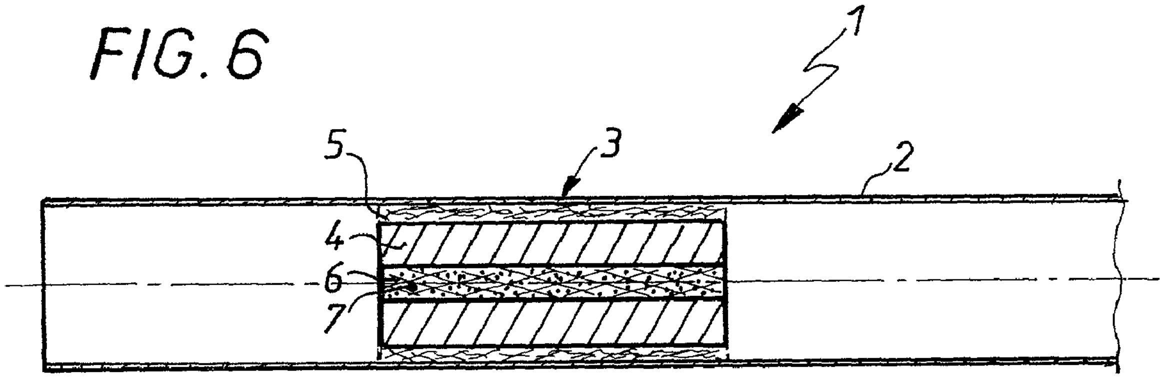
FIG. 6 is a partial view of a sixth embodiment of a straw of the invention.

Referring to FIG. 6, the straw 1 comprises a segment of tube 2 fitted at one end with a one-piece stopper 3.

The stopper 3 comprises a thermoplastics material core 4 sheathed with filaments constituting a sheath 5 and comprising a central braid 6 of synthetic filaments impregnated with gel powder 7.

The filaments constituting the sheath 5 are impregnated with gel powder.

The person skilled in the art will understand that although the invention is described and illustrated with respect to particular embodiments, many variants thereof can be envisaged that remain within the scope of the invention as defined by the accompanying claims.

There is claimed:

1. A straw for the conservation of small quantities of substances, in particular biological substances, said straw comprising a segment of tube and a stopper provided inside one end of said segment of tube, said stopper including gel powder and a second component that holds the gel powder in place, wherein the gel powder contacts the tube segment and swells when contacted by the substance to adhere to the tube segment and said second component comprises a thermoplastics material core sheathed with filaments constituting a sheath.

2. The straw claimed in claim 1, wherein said filaments of said sheath are synthetic filaments.

3. The straw claimed in claim 2, wherein said synthetic filaments are polyester filaments.

4. The straw claimed in claim 1, wherein said sheath takes the form of a braid.

5. The straw claimed in claim 1, wherein said stopper is a three-part stopper comprising an external part which is not in direct contact with said substance contained in said straw, an internal part which is constituted by said second component and is in contact with said substance contained in said straw, and an intermediate part between said external and internal parts and consisting of said gel powder.

6. The straw claimed in claim 5, wherein said external part comprises a second thermoplastics material core sheathed by filaments constituting a second sheath.

7. The straw claimed in claim 5, wherein said external part comprises a fibrous substance plug.

8. The straw claimed in claim 7, wherein said core is provided with a bore.

9. The straw claimed in claim 8, further comprising a central braid in said bore of said core.

10. The straw claimed in claim 1, wherein said stopper is a one-piece stopper.

11. The straw claimed in claim 10, wherein said sheath is impregnated with said gel powder.

12. The straw claimed in claim 10, wherein said core is provided with a bore, said straw further comprises a central braid, said sheath is impregnated with a first portion of said gel powder and said braid is imprgnayed with a second portion of said gel powder.

13. The straw claimed in claim 1, wherein said filaments of said sheath are white.

14. The straw claimed in claim 1, wherein said filaments of said sheath are colored, constituting a color-coded indicator of the contents of said straw.

15. The straw claimed in claim 1, wherein said core is colored, constituting a color-coded indicator of the contents of said straw.

16. The straw claimed in claim 1, wherein said gel powder is colored, constituting a color-coded indicator of the contents of said straw.

17. The straw claimed in claim 1, wherein said gel powder is selected from alginates and polyvinyl alcohol.

* * * * *